United States Patent
Cebolla Ramirez et al.

(10) Patent No.: US 8,283,125 B2
(45) Date of Patent: Oct. 9, 2012

(54) PEPTIDE AND PROTEIN PRESERVATION METHOD

(75) Inventors: Angel Cebolla Ramirez, Sevilla (ES); Moisés Alvarez Maqueda, Sevilla (ES)

(73) Assignee: Biomedal, S.L., Sevilla (ES)

( * ) Notice: Subject to any disclaimer, the term of this patent is extended or adjusted under 35 U.S.C. 154(b) by 321 days.

(21) Appl. No.: 12/682,690

(22) PCT Filed: Sep. 5, 2008

(86) PCT No.: PCT/ES2008/000579
§ 371 (c)(1), (2), (4) Date: May 26, 2010

(87) PCT Pub. No.: WO2009/034204
PCT Pub. Date: Mar. 19, 2009

(65) Prior Publication Data
US 2010/0256301 A1    Oct. 7, 2010

(30) Foreign Application Priority Data
Sep. 11, 2007    (ES) .................................. 200702475

(51) Int. Cl.
*G01N 33/53*    (2006.01)
(52) U.S. Cl. ........................................................ 435/7.1
(58) Field of Classification Search .................... 435/7.1
See application file for complete search history.

(56) References Cited

U.S. PATENT DOCUMENTS

| | | | |
|---|---|---|---|
| 5,998,155 A * | 12/1999 | Burton et al. | 435/7.5 |
| 6,268,191 B1 * | 7/2001 | Prud'homme et al. | 435/178 |
| 2004/0229330 A1 | 11/2004 | Bettencourt et al. | |
| 2005/0112603 A1 | 5/2005 | Kuo et al. | |

OTHER PUBLICATIONS

Pearcy et al. 2000; Lyophilization processing: Freeze-dried microspheres offer new IVD packaging and product opportunities, www.ivdtechnology.com.*

* cited by examiner

*Primary Examiner* — Karen Cochrane Carlson
(74) *Attorney, Agent, or Firm* — Arent Fox LLP (57) ABSTRACT

The invention relates to a method for preserving peptides or proteins over long periods of time. The invention also relates to the use of the preservation method for the transport of labeled peptides or proteins without requiring refrigeration, as well as to a set of tools for implementing said method.

15 Claims, 7 Drawing Sheets

PEPTIDE AND PROTEIN PRESERVATION METHOD

CROSS-REFERENCE TO RELATED APPLICATION

This application is a National Stage entry of International Application No. PCT/ES2008/000579, filed Sep. 5, 2008, which claims priority to Spanish Patent Application No. P200702475 filed Sep. 11, 2007. The disclosure of the prior application is hereby incorporated in it's entirety by reference.

TECHNICAL FIELD

The technical field that encompasses this invention is the biotechnological, and it is applied in the area of preservation and transport of peptides and proteins and is used for health, diagnosis, pharmaceutical, agronomic or industrial purposes. It is also used in the field of life sciences research.

STATE OF THE ART

Peptides or proteins are generally unstable when preserved at room temperature (approximately 25° C.) in liquids or aqueous solutions; thus in few hours, the phenomenon of deterioration, de-naturalization and or growth of microbial contaminants begins to appear (Jaenicke, R., (2000). *J Biotechnol*, 79, 193-203; Meyer, J. D., et al (2002). *Pharm Biotechnol*, 13, 85-107). For the purpose of avoiding these phenomena, diverse methods of peptides and protein preservation are used; the most common may be summarized as: (i) preservation at refrigerated temperature; (ii) addition of stabilizing agents; and, (iii) dehydration or lyophilization.

Traditionally the peptides or proteins have been preserved in an aqueous solution at refrigerated temperature, either in liquid form at 4° C. or frozen at −20° C. This way, the speed with which the degradation reaction occurs is reduced. However, the processes of repeatedly freezing and thawing causes alterations in the structure and or activity of the peptides and proteins (Tang, X. C., et al (2005). *Pharm Res*, 22, 1167-1175). Likewise, the peptides and proteins preserved in this way do not prevent the phenomena of degradation, denaturation and/or microbial contamination from appearing.

The stabilizing agents are inert substances that modify the physical-chemical characteristics of the aqueous solutions used to preserve peptides and proteins, thus reducing the risk of degradation. Examples of these agents are: glycerol, sugars (glucose, galactose, sucrose, trehalose), polyethylene glycols, amino-acids (methionine, histidine), detergents (Triton X-100, Tween-20), and other proteins (albumin) (Arakawa, T., (1991). *Pharm Res*, 8, 285-291; Crowe, J. H., et al (1987). *Biochem J*, 242, 1-10; Levine, R. L. (1983). *J Biol Chem*, 258, 11828-11833). Glycerol is a traditional stabilizing agent that reduces the freezing point of the aqueous solution containing the peptides and proteins, enabling their preservation in liquid state without low temperature freezing (−20° C.) (Schamagl, C., et al (2005). *Biochim Biophys Act*, 1749, 187-213). The stabilizing agents are usually used alongside other preservation methods of peptides and proteins (Carpenter, J. F. et al (1987). *Biochim Biophys Act*, 923, 109-115). Nonetheless, the stabilizing agents often may interfere in the subsequent activity or application of the peptide or protein of interest and must be eliminated using dialysis systems or other more aggressive procedures (saline or acid pouring) that alter this peptide or protein (Prive, G. G. (2007) *Methods*, 41, 388-397).

Lyophilization is a dehydration process in which the water molecules are eliminated from a frozen sample inside a vacuum system This preservation method requires that the peptide or protein, which is dissolved in aqueous matter or solution be frozen; preferably quickly. A procedure used to quickly freeze the peptide or protein solution consists of immersing it in liquid nitrogen. Then, a vacuum is applied to the frozen sample, which causes the sublimation or vaporization of the frozen phase at below zero temperatures (primary dehydration). The residual humidity may be eliminated afterwards, which enables the temperature to be gradually increased (secondary dehydration). The results of the lyophilization process is a dust or dry and crystalline substance that contains the peptide or protein to be preserved (Randolph, T. W., (1997). *J Pharm Sci*, 86, 1198-1203; Wang, W. (2000). *Int J Pharm*, 203, 1-60). In lyophilization, during the primary and secondary dehydration phases, the peptides or proteins undergo physical and chemical changes, like increasing of the saline concentration, aggregation/precipitation, physical stress, extreme pH, which produces alterations in its structure and/or activity. Additionally, lyophilized peptides or proteins are usually more hygroscopic, and tend to absorb ambient humidity, which also causes degradation phenomenon and a decrease in the activity of these peptides or proteins (Webb, S. D., et al (2003). *J Pharm Sci*, 92, 715-729).

The affinity labels (tags) have become a commonly used system for purifying proteins and native protein complexes for obvious reasons: they enable to purify or enrich these peptides or proteins from creed extracts, hundreds to thousands of times in one single step, without needing to previously eliminate nucleic acids or other cellular material; and they especially allow using general purification protocols with a broad diversity of proteins, in contrast with the design and preparation of specific protocols for each peptidic matter requiring conventional chromatography (Waugh, D. S., (2005). *Trends Biotechnol*, 23, 316-320; Esposito, D. et al (2006). *Curr Opin Biotechnol*, 17, 353-358). Thanks to these advantages, purification using affinity labels has provided investigators with the production of a multitude of recombinant proteins, which are of interest in research and diagnosis, and is the most commonly used procedure in high performance projects (Braun, P., et al. (2002) PNAS; 99, 2654-2659).

Currently, the scientific collaborations or client-supplier specialized services require the exchange or shipment of peptides or proteins used for health, diagnosis, pharmaceutical, agronomic, and industrial purposes or for life sciences research purposes, between public centre laboratories or private businesses located in the same country or in different countries. One of the problems encountered with shipping these materials is preventing the deterioration and denaturation phenomenon and/or growth of the above mentioned microbial contaminants. The most common transport system consists in using large boxes filled with ice, dry ice or cold packs to guarantee that the peptides or proteins are preserved at a cool temperature during the time established for transportation (from 24 hours to 4-5 days for this type of shipment). These systems are cumbersome and result in a high economic cost. Also, any delay in the transportation time (detained at customs, messenger delays, etc) causes the material to reach its destination at room temperature, which causes the material to be returned unless the customer verifies that the shipped materials are still in good condition. Therefore, new methods are required that enable to resolve the problem of preservation and transport of peptides or proteins at room temperature. This invention describes a simple, economic and versatile method aimed at resolving this problem, as well as the necessary tools to accomplish it.

DETAILED DESCRIPTION OF THE INVENTION

The purpose of this invention relates to a method of preserving tagged peptides or proteins for several days and even months without requiring refrigeration, and its employment in storage and transport of peptides and proteins used in the health, diagnosis, pharmaceutical, agronomic or industrial sectors. This invention describes an alternate method that is safer and more convenient than the currently existing methods, such as preservation and/or transport of peptides or proteins in an aqueous solution at a chilled temperature or lyophilization. (Tang, X. C., et at (2005). *Pharm Res*, 22, 1167-1175; Webb, S. D., et at (2003). *J Pharm Sci*, 92, 715-729). Thus, the purpose of the invention encompasses the use of derivatized solid matrices with compounds that have an affinity for specific sequences or tags present in the peptides or proteins that are to be preserved.

This invention's method of preserving peptides or proteins includes the following stages:

(a) flow of a fluid or solution containing the tagged peptide or protein through a solid or semi-solid, porous, derivatized matrix, in such a state that the peptide or protein tag binds by affinity to the functional groups that are present in said matrix.

(b) flow of a cleaning solution through the matrix in order to eliminate the biological material, peptides or proteins, or other substances from the fluid or solution that are not attached to the derivatized, solid or semi-solid, porous matrix.

(c) partial or total drying of the matrix, with the peptide or protein immobilized at moderate temperature (starting at 15° and no higher than denaturizing temperatures, preferably from 18 to 42° C.), preferably at room temperature.

(d) matrix preservation with the peptide or protein immobilized inside a wrapping that is clean and septic during the time required prior to its use.

(e) recovery of the immobilized peptide or protein, by passing a solution through the matrix that is comprised of specific compounds that interrupt the affinity binding between the peptide or protein tag and the functional groups of the derivatized, solid or semi-solid porous matrix.

This invention specifically describes the use of solid or semi-solid matrices comprised of any porous, fibrous or reticular matter that allows liquids to flow through them, preferably one of the following materials or their derivatives: cellulose, agarose, polyacrylates, polymetracrylates, polyvinyls, chitosans, polystyrenes and any polymer, natural or of derivatized synthesis, with a porous or fibrous structure. In general, any polymer may be used that is characterized for having a high surface/volume ratio and that is commonly used as solid or semi-solid supports in affinity chromatography for the purification of peptides or proteins. Likewise, these matrices are described as derivatized with compounds that have an affinity for specific sequences or tags that are present in the peptides or proteins to be preserved. Specifically, the attachment to the matrix is performed through an area of the peptide or protein that would not affect its activity or functionality, since the tags usually bind to the amino end or carboxyl terminal of the peptide or protein, keeping enough distance from the active areas prevent both domains or regions from interacting.

Preferably the derivatized matrices would be used along with some of the following compounds: iminodiacetic acid (IDA) or nitrilotriacetic acid (NTA) attached to dicationic metals such as nickel (Ni), cobalt (Co) or copper (Cu); tertiary amines or quaternary as the diethylaminoethanol (DEAF) or the trimethyl ammonium (QAE); glutathione; amylose; avidin or streptavidin; calmodulin; protein A; protein G; or any other compound permits the purification via affinity chromatography of peptides and proteins that are known by experts in the field. The labels or tags that allow the affinity binding to functional groups that are present in the matrices, preferably may be Histidine tags (Histag), domains of choline binding, glutathione S-transferase (GST-tag), maltose binding protein (MBP-tag), biotin or Strep-tag, calmodulin binding domain (CBD-tag) or calmodulin binding protein (CBP-tag) or calmodulin regulated proteins, total or partial sequences of immunoglobulin heavy chains, or any other type of label that allows the purification by affinity chromatography of peptides or proteins that are known to experts in this field.

This invention also states that the peptides or proteins preserved in the matrices can be recovered into an aqueous solution via the passing of a solution with specific compounds through the matrix, which interrupts the affinity binding between the peptide or protein tag and the functional groups of the solid or semi-solid derivatized matrix. Preferably some of the following compounds would be used: Imidazole; coline; glutathione; maltose; biotin; calcium chelating agents; acid solutions; or any other compound that allows the elution of peptides or proteins that are bound by affinity to chromatographic supports, which are known to experts in the field.

From the method used for preserving peptides or proteins and from a variety of previously described compounds, some of the configurations listed in the following table may be used:

| Tag* | Derivatized Matrix** | Recovery*** |
|---|---|---|
| Histag | IDA —Ni, —Co, —Cu<br>NTA —Ni, —Co, —Cu | Imidazole |
| Lytag | DEAE or QAE | Coline |
| GST-tag | Glutathione | Glutathione |
| MBP-tag | Amilose | Maltose |
| Biotin or Streptag II | Avidina or Streptavidin | Biotin |
| CBD-tag or CBP-tag | Calmodulin | Calcium Chelating |
| Inmunoglobulines | Protein A or Proteina G | Acid solutions |

*specific sequences or tags present in the peptide or protein.
**compounds used to derivatize the matrix.
***compounds that interrupt the binding of the peptide or protein and the matrix.

The most innovative and favourable characteristics of this invention can be summarized in the following paragraphs:

1. The immobilization of peptides or proteins in solid or semi-solid matrices that are partially or totally dehydrated, allows for the preservation at room temperature of said peptides or proteins for periods ranging from a few hours to a few months (approximately 18-25° C.) without requiring refrigeration. In the same way, a large proportion of peptides or proteins could be preserved for longer periods of time at lower temperatures.

2. The use of solid or semi-solid derivatized matrices enables to directly preserve the tagged peptides or proteins that have been previously purified, or are contained in cell extracts that express them or any other non-purified soluble format.

3. Against other methods of peptide or protein preservation, the described method has the advantage that it can be carried out in a short period of time and does not require large or costly instruments.

4. The described method avoids the processes of freezing-thawing, which may cause alterations in the structure and/or activity of the peptides and proteins to be preserved as well as the physical-chemical changes and the hygroscopicity phenomenon that appears during the lyophilization processes.

5. The described method also avoids using stabilizing agents that may interfere with the subsequent application of the peptide or protein.

By using common techniques in biochemical laboratories, this invention also includes the use of a set of tools (kits) or devices that enable to carry out the preservation of the tagged peptides or proteins, which are characterized because they include:

(a) a solid or semi-solid porous matrix, derivatized in the form of a membrane for immobilization of the tagged peptide or protein.

(b) a support to contain the matrix, through which the different used fluids or solutions will flow, with the dimensions and water tightness required for the matrix to fit and to force the fluid to necessarily pass through its derivatized surface.

(c) tubes or syringes that are attachable to the base and used for inserting the fluid or solution containing the tagged peptide or protein, the matrix cleaning solution, and the recovery solutions with specific components that interrupt the affinity binding between the peptide or protein tag and the functional groups of the solid or semi-solid derivatized matrix.

Figure 1:
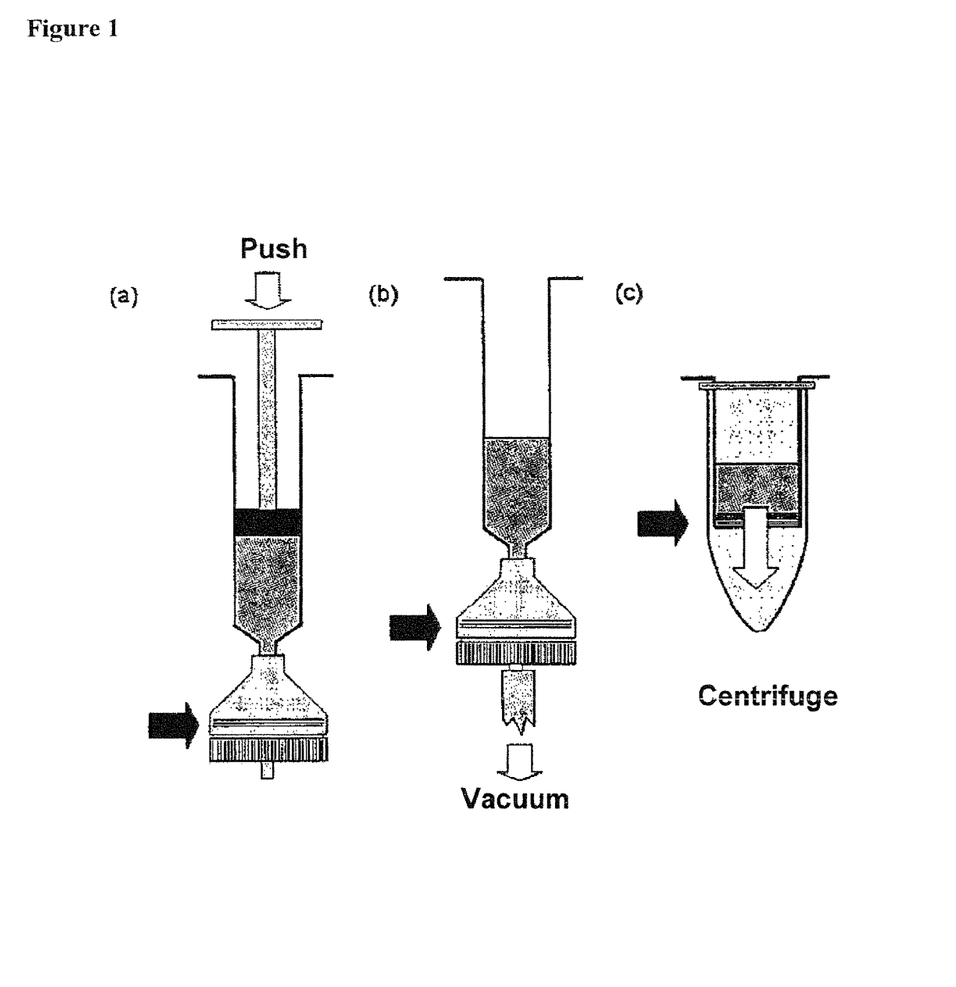
FIG. 1. Sequence reflecting different ways of passing the fluid or solution containing the tagged peptide or protein through the derivatized matrix. A support with the matrix inside may be used, to which a syringe with a piston is attached, used for inserting the fluid or solution and exerting the required pressure (a); a support with the matrix inside and with an output to a vacuum system that exerts the required pressure, to which a syringe is attached, which is used for inserting the fluid or solution (b); or a support with the matrix inside, adaptable to a tube compatible with centrifugation systems in order to exert the required pressure (c). The black arrow shows where the matrix is placed in each of the examples.

(d) a device that enables to exert the pressure required so that the different used fluids or solutions pass through the matrix, which may for example be: a piston attached to the syringe (FIG. 1a); a support output that is attachable to a vacuum system (FIG. 1b); a tube that is attachable to a support which is compatible with centrifuge systems (FIG. 1c).

(e) wrapping for the preservation and/or shipment of a matrix with the immobilized peptide or protein.

(f) matrix cleaning solution.

(g) recovery solutions with specific components that interrupt the affinity binding between the peptide or protein tag and the functional groups of the derivatized solid or semi-solid matrix.

Likewise, the purpose of the invention encompasses using this method, using the aforementioned kits or devices for preserving and/or transporting peptides or proteins used in the fields of health, diagnosis, pharmaceutics, agronomic and industrial or in the life sciences research field, without needing refrigeration for the purpose of:

1. preserving peptides or proteins that will be used in studies as samples or controls during biological, immunological, biochemical or analytical tests.
2. exchanging peptides or proteins of interest between public centre laboratories or private companies.
3. sending of peptides or proteins used to immunize laboratory animals for the purpose of obtaining antibodies against said peptides or for vaccine research.

EMBODIMENT THE INVENTION

Example 1

Preservation and Recovery of a Fluorescent Protein (GFP) Tagged with Histidine Tags Inside Derivatized Membranes This example describes how to preserve at room temperature and for long periods of time, labelled proteins with histidine tags (Histag) inside derivatized membranes with functional groups that have an affinity for said tag.

The membranes used in this example are shaped like discs that are 2.5 cm in diameter and 0.65 mm wide, and are derivatized with DA-Ni. First, four membrane discs are placed inside a propylene support for filtration of the proper dimensions (support de filter swinnex polipropilene, Millipore) and are washed with 10 ml of cleaning solution comprised of 50 mM of potassium phosphate buffer Ph 8.0, 300 mM NaCl and 10 mM of imidazole, using a syringe attached to the support.

The protein to be preserved, 1 mg of green fluorescent protein (GFP) fused from its carboxyl terminal end to a Histag (GFP-Histag), is dissolved in 10 ml of cleaning solution and passed twice through the support with the membrane discs, using the attached syringe. Afterwards, the membrane discs are cleaned using 25 ml of cleaning solution. Then the support membrane discs are extracted and dried at room temperature for at least 30-60 min in a clean environment (laminar flow hood, petri plate, etc.). These membrane discs with the immobilized protein are inserted in a petri plate and are sent to another laboratory at room temperature and by way of conventional mail-messenger services, where after 15 days it is utilized by a different user in the next testing phase.

Figure 2:
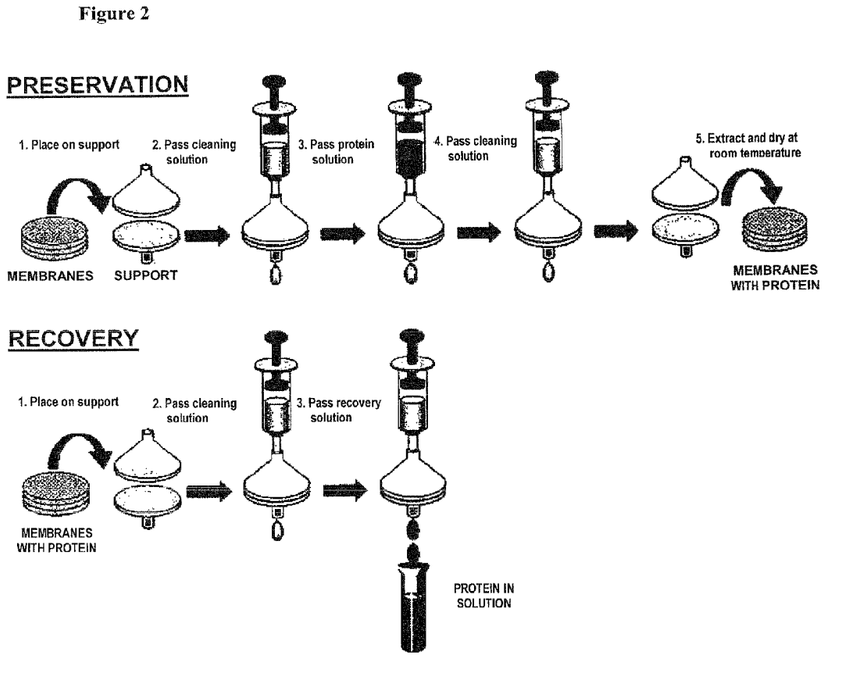
FIG. 2. General sequence of the method of preservation and recovery of tagged proteins in derivatized membranes.
Figure 3:
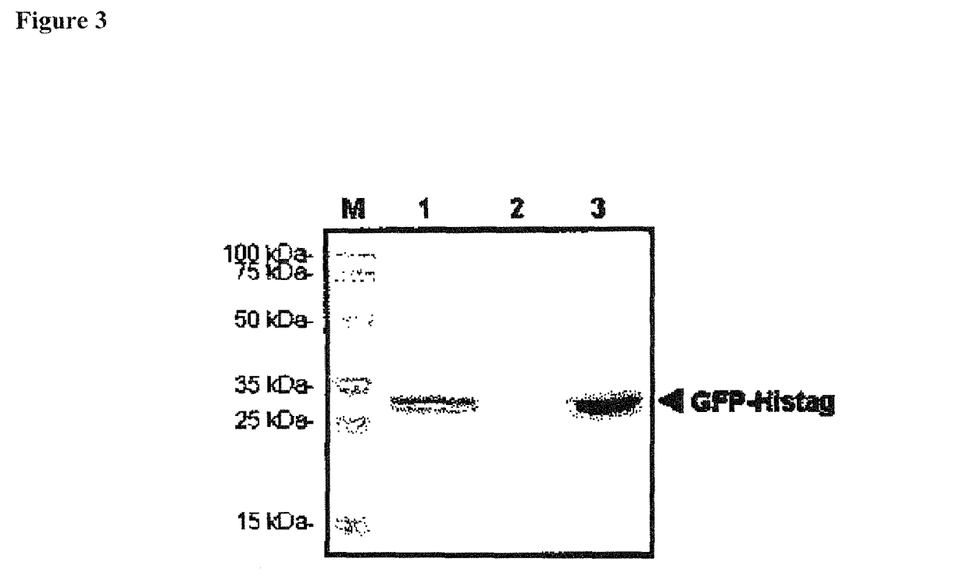
FIG. 3. Preservation and recovery of GFP-Histag in derivatized membranes with IDANi. Molecular weight marker (M); GFP-Histag solution before passing through the membrane discs (1) and after passing through the membrane discs (2); GFP-Histag solution recovered from the membrane discs (3).

To recover the immobilized proteins in the membrane discs, these are placed inside the support and are washed with 10 ml of the cleaning solution, using the syringe attached to the support. Finally, 5 ml of a recovery solution comprised of 50 nM of potassium phosphate buffer pH 8.0, 300 mM NaCl and 250 mM of imidazole are passed through the support with the membrane discs using the attached syringe and collecting the results inside clean tube. FIG. 2 shows a general schematic of the procedure and materials used. FIG. 3 shows the results of this example, analyzed by SDS-PAGE in gels with 12% acrylamide, stained with Coomassie. As may be observed, almost the entire GFP-Histag is immobilized as it flows through the membrane discs and can easily be recovered to solution by passing the recovery solution through the membrane discs.

Example 2

Immobilization, Storage, and Release of Protein A Tagged with Choline Binding Domains in Derivatized Membranes This example describes how to preserve at room temperature and for long periods of time, proteins tagged with choline binding domains (Lytag) within derivatized membranes with functional groups that have an affinity for said tag.

The membranes used in this example are shaped like discs that are 2.5 cm in diameter and 0.2 mm wide and are derivatized with DEAE (diethylaminoethyl). First, six membrane discs are placed inside a propylene support for filtration of the proper dimensions (support de filter swinnex polipropilene, Millipore) and are washed with 10 ml of cleaning solution comprised of 20 mM of potassium phosphate buffer pH 7.0, 300 mM NaCl and 5 mM of choline chloride using a syringe that is attached to the support.

The protein to be preserved, 1 mg of protein A fused at its amino terminal ending to a Lytag (Lytag-protein A) using Biomedal commercial kit, is dissolved in 10 ml of cleaning solution and is passed two times through the support with the membrane discs, using the attached syringe. Afterward, the membrane discs are cleaned using 25 ml of cleaning solution. Then, the membrane discs are extracted from the support and are dried at room temperature for at least 30-60 min in a clean environment (laminar flow hood, petri plate, etc) These membrane discs with the immobilized protein are inserted in a petri plate and sent at room temperature to another laboratory, via conventional, mail-messenger systems; and after 15 days have elapsed, they are used by a different user in the next test phase.

Figure 4:
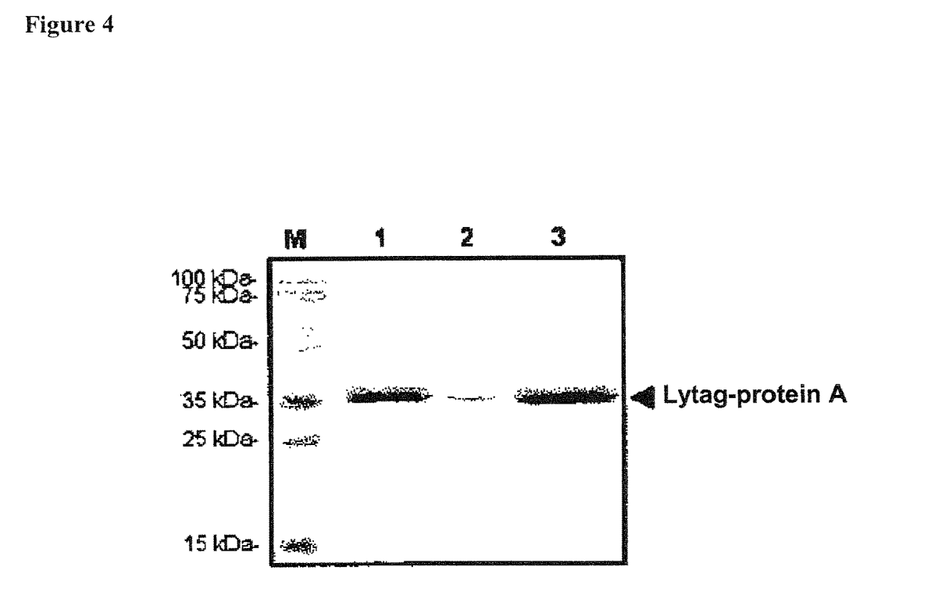
FIG. 4. Preservation and recovery of Lag-protein A in derivatized membranes with DEAE. Molecular weight marker (M); Lag-protein A solution before passing through the membrane discs (1) and after passing through the membrane discs (2); Lag-protein A solution recovered from the membrane discs (3).

To recover the immobilized protein in the membrane discs, these are placed inside the support and are washed with 10 ml of the cleaning solution, using the syringe attached to the support. Finally, 5 ml of a recovery solution comprised of 20 nM of potassium phosphate buffer pH 7.0, 300 mM NaCl and 250 mM of choline chloride are passed through the support with the membrane discs using the attached syringe and collecting the result inside a clean tube. FIG. 4 shows the results of this example, analyzed by SDS-PAGE in gels with 12% acrylamide, stained with Coomassie. As seen above, almost all the fusion polypeptide, Lytag-protein A, is immobilized as it passes through the membrane discs, and can be recovered easily to solution by passing the recovery solution through the membrane discs.

Example 3

Activity of the Fluorescent Proteins Tagged with Choline Binding Domains, Preserved and Recovered from Derivatized Membranes This example describes how proteins tagged with choline binding domains (Lytag) maintain their structure and/or activity when preserved immobilized at room temperature for long periods of time in derivatized membranes with functional groups that have affinity for the label, and also when they are once again recovered to aqueous solution.

The fluorescent proteins used, GFPmut3, ECFP, EYFP y EGFP (Cormack, B. P., et al (1996). Gene, 173, 33-38; Heim, R., et al (1994) Proc Natl Acad Sci, 91, 12501-12504; Ormö, M. et al (1996) Science, 273, 1392-1395; Prasher, D. C., et al (1992) Gene, 111, 229-233), were fused at their amino terminal end to a Lytag (Lytag-GFPmut3; Lytag-ECFP; Lytag-EYFP; and Lytag-EGFP) and expressed in E. coli using the commercial Biomedal CASCADE-LYTAG system. The membranes used in this example are shaped like discs that are 2.5 cm in diameter and 0.2 mm wide and are derivatized with DEAE. First, four membrane discs are placed inside a propylene filtration support of the proper size (support de filtre swinnex polipropilene, Millipore) and are washed with 10 ml of cleaning solution comprised of 20 mM of potassium phosphate buffer pH 7.0, 300 mM NaCl and 5 mM of choline chloride, using a syringe that is attached to the support.

Figure 5:
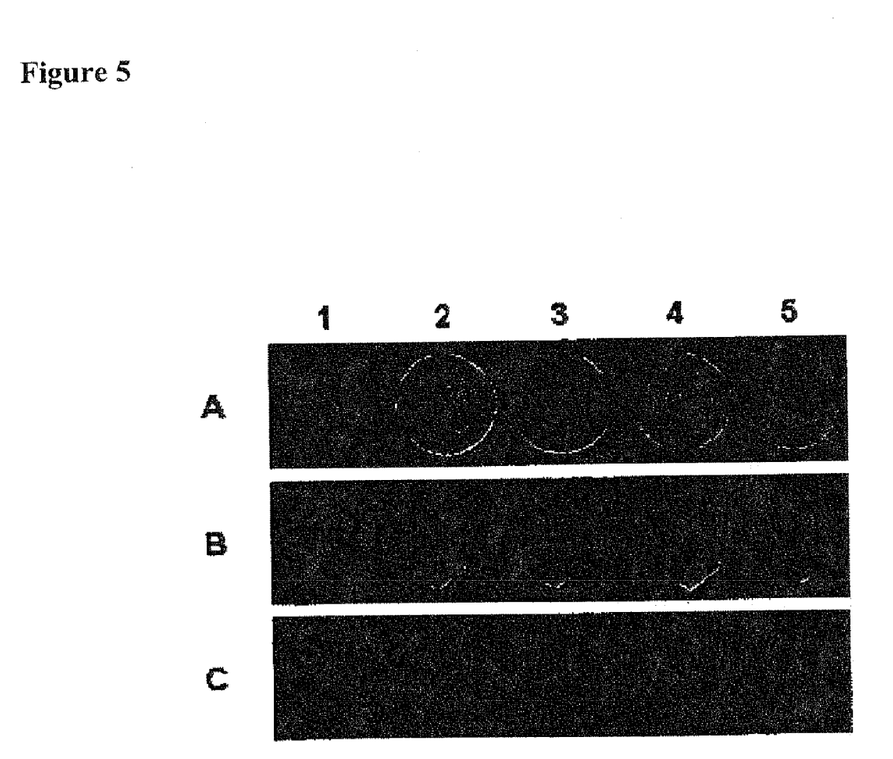
FIG. 5. Activity of fluorescent proteins preserved and recovered in derivatized membranes with DEAE. Fluorescent proteins: control without proteins (1); Lytag-GFPmut3 (2); Lytag-ECFP (3); Lytag-EYFP (4); and Lytag-EGFP (5). Membrane discs with the different fluorescent immobilized proteins (A). Aqueous solutions with the different fluorescent proteins recovered from the membrane discs (B). Membrane discs after aqueous solution recovery of the different fluorescent proteins (C).

Extracts from cultures of E. coli that super-express the different fluorescent proteins fused to Lytag, are passed two times through the support with the membrane discs, using the attached syringe. Afterwards, the membrane discs are cleaned using 25 ml of cleaning solution. Then, the membrane discs are extracted from the support and are dried at room temperature for at least 30-60 min in a clean environment (laminar flow hood, petri plate, etc) These membrane discs with the different immobilized fluorescent proteins are preserved at room temperature for 24 hours. After this period of time the fluorescence of the proteins is analyzed by observing them under an ultraviolet lamp. Afterwards, these membrane discs are placed along with the different immobilized fluorescent proteins inside the support and are washed using 10 ml of cleaning solution, using a syringe that is attached to the support. Subsequently, 2 ml of the cleaning solution is passed through the support with the membrane discs, comprised of 20 mM of potassium phosphate buffer pH 7.0, 300 mM NaCl and 250 mM of choline chloride, using the attached syringe and collecting the results inside clean tubes. These tubes, with the different fluorescent proteins in aqueous solution as well as the used membrane discs, are analyzed under an ultraviolet lamp. FIG. 5 shows the results of this example. As can be observed, the different fluorescent proteins maintain their structure and/or activity when preserved in the derivatized membranes, and also when they are once again recovered to aqueous solution.

Example 4

Preservation and Recovery of an Antibody or Immunoglobulin in Derivatized Membranes with Immobilized Protein A This example describes how to preserve at room temperature for long periods of time, antibodies or immunoglobulin in derivatized membranes with immobilized protein A.

The membranes used in this example are shaped like discs that are 2.5 cm in diameter and 0.2 mm wide, and are derivatized with DEAE (diethylaminoethyl). First, three membrane discs are placed inside a propylene filtration support of the proper size (support de filtre swinnex polipropilene, Millipore) and are washed with 10 ml of an immobilization solution comprised of 20 mM of potassium phosphate buffer pH 7.0, 300 mM NaCl and 5 mM of choline chloride, using a syringe that is attached to the support Subsequently, 1 mg of protein A fused by its amino terminal end to a Lytag (Lytag-protein A) is dissolved in 10 ml of the immobilizing solution and is passed two times through the support with the membrane discs, using the attached syringe Afterwards, the membrane discs are cleaned using 25 ml of immobilizing solution. These membrane discs with immobilized Lytag-protein A are used to preserve antibodies and immunoglobulins.

The monoclonal antibody to be preserved, 2.5 mg of mouse immunoglobulin $IgG_{2a}$, is dissolved in 10 ml of a cleaning solution comprised of 20 mM of potassium phosphate buffer pH 7.0 and is passed four times through the support with the membrane discs containing immobilized Lytag-protein A, using the attached syringe. Afterward, the membrane discs are cleaned using 20 ml of cleaning solution. Then, the membrane discs are extracted from the support and are dried at room temperature for at least 30-60 min in a clean environment (laminar flow hood, petri plate, etc) These membrane discs with the immobilized antibody or immunoglobulin are preserved at room temperature for 24 hours.

Figure 6:
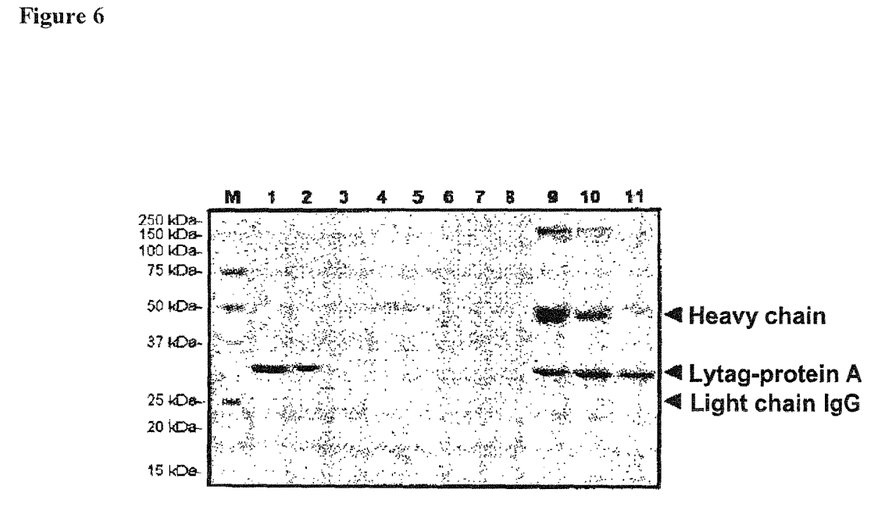
FIG. 6. Preservation and recovery of an antibody or immunoglobulin in derivatized membranes with immobilized protein A. Molecular weight marker (M); Lag-protein A solution before passing through the membrane discs (1) and after passing through the membrane discs (2); washing of immobilized protein A membrane discs. (3); antibody or immunoglobulin solution (IgG) before passing through the membrane discs with immobilized protein A (4) and after passing through the immobilized protein A membrane discs (5); $1^{st}$ $2^{nd}$ and $3^{rd}$ washing of membrane discs with immobilized antibody or immunoglobulin (6-8); different fractions of membrane discs with recovered antibody or immunoglobulin (9-11).

In order to recover immobilized antibody or immunoglobulin in the membrane discs, these are placed inside the support and are washed using 10 ml of cleaning solution, using the syringe attached to the support. Finally, 6 ml of a recovery solution comprised of 1 M of Tris-HCl pH 9.0, is passed through the support with the membrane discs, using the attached syringe and collecting the results in 2 ml fractions. FIG. 6 shows the results of this example, analyzed by SDS-PAGE in gels with 10% acrylamide, stained with Coomassie. As can be observed: (i) in the first phase of testing, the saturation of the membrane discs with Laytag-protein A is achieved to prevent unspecified interactions between the antibody and the membrane discs; (ii) an important portion of the antibody or immunoglobulin is immobilized during its passage through the membrane discs with Laytag-protein A; (iii) said antibody or immunoglobulin can be recovered to solution by passing the recovery solution through the membrane discs.

The LYTAG-protein A could previously be immobilized to the membrane through the activation of a covalent binding to the membrane by conjugating agents, which are known to experts in the field. This way, the antibody can be detached from the membrane without this protein, using a pH acid solution and deceiving the immunoglobulin in a buffered solution.

Example 5

Stability of the β-Galatosidase Tagged with Histidine Tags, Preserved in Derivatized Membranes This example describes how proteins tagged with histidine tags (Histag) maintain their structure and/or activity when preserved at room temperature and for long periods of time, in derivatized membranes with functional groups that have affinity for said tag.

Figure 7:
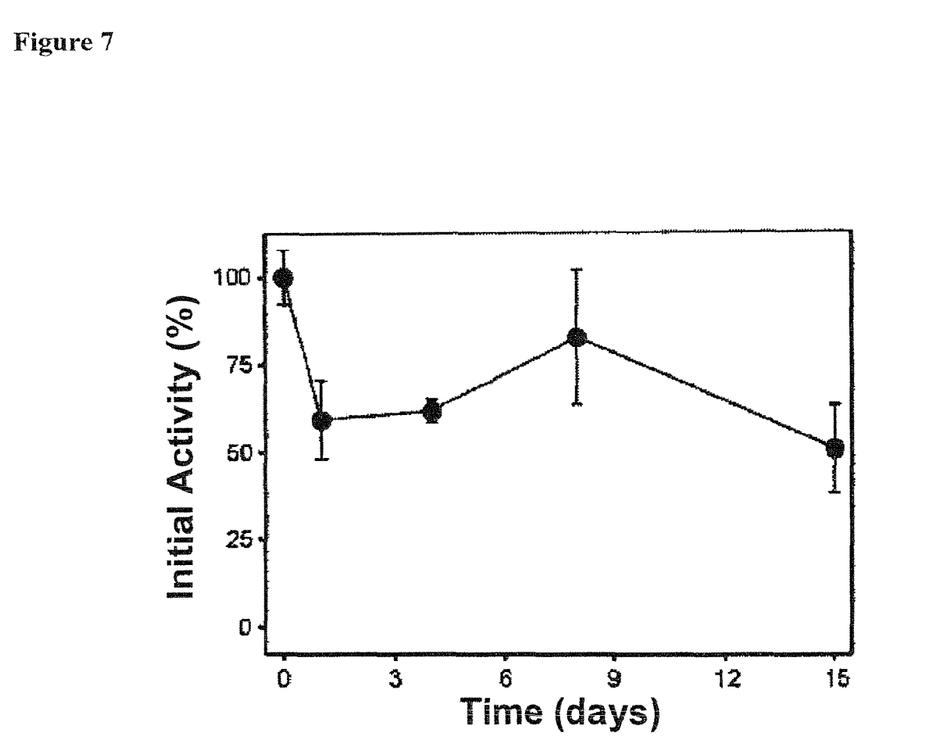
FIG. 7. Stability of Histag-β-galactosidase preserved in derivatized membranes.

The membranes used in this example are shaped as laminates that are adaptable to Vacuum Manifold equipment to produce Dot-Blot, and are derivatized with DA-Ni. First, the membrane sheets are incubated for 10 mM at room temperature in a cleaning solution comprised of 50 mM of potassium phosphate buffer pH 8.0, 300 mM NaCl and 10 mM of imidazole. Subsequently, the membrane sheets are placed inside the Vacuum Manifold equipment with adaptor to produce Dot-Blot connected to a vacuum system, and then through each of the wells, 0.2 ml of the *E. coli* culture extracts are passed that superexpress β-galactosidase fused at its amino terminal end to a Histag (Histag-β-galactosidase). Afterwards, the wells are cleaned using 4 ml of cleaning solution. Then the membrane sheets of the Vacuum Manifold equipment are extracted and are dried at room temperature for at least 30-60 min in a clean environment (laminar flow hood). Each of the dots is cut in equally sized segments and is preserved at room temperature until they are used in the β-Galactosidase activity test. FIG. 7 shows that the Histag-β-Galactosidase preserved in membrane laminates, maintains at least 50% of its initial activity after 15 days at room temperature.

The invention claimed is:

1. A method for preserving or storing tagged peptides or proteins by means of their reversible binding to solid or semi-solid derivatized matrices, said method comprising:
   (a) passing a fluid or solution that contains the tagged peptide or protein through a solid or semi-solid porous matrix having functional groups, wherein the tag of the peptide or protein binds by affinity to functional groups that are present in the matrix,
   (b) passing a cleaning solution through the matrix to eliminate biological material, peptides or proteins, or other substances of the fluid or solution not bound to the solid or semi-solid derivatized, porous matrix,
   (c) partially or totally drying the matrix comprising the tagged peptide or protein at moderate temperature from 12° to 60° C.
   (d) placing the partially or totally dried matrix comprising the tagged peptide or protein inside a wrapping that is clean and septic during the time required prior to its user, and
   (e) recovering the tagged peptide or protein from the matrix by passing a solution through the matrix that comprises specific compounds that interrupt the affinity binding between the peptide or protein tag and the functional groups of the solid or semi-solid porous matrix.

2. The method for preserving tagged peptides or proteins according to claim 1, wherein the matrices are derivatized by compounds with an affinity for the tags that are present in the peptides or proteins.

3. The method for preserving tagged peptides or proteins according to claim 1, wherein the matrix is comprised of porous, fibrous or reticular material that allows liquids to flow through it.

4. The method for preserving tagged peptides or proteins according to claim 1, wherein the matrix is comprised of a polymer having a high surface/volume ratio and are used as solid or semi-solid purification supports in affinity chromatography for the purification of peptides or proteins.

5. The method for preserving tagged peptides or proteins according to claim 1, wherein the matrix comprises one or more materials or its derivatives selected from the group consisting of, cellulose, agarose, polyacrylates, polymetracrylates, polyvinyls, chitosans, polystyrenes, and any polymer that is porous or has fibrous structure.

6. The method to preserve tagged peptides or proteins according to claim 1, wherein the matrix is comprised of cellulose or any of its derivatives.

7. The method for preserving tagged peptides or proteins according to claim 1, wherein the matrix is derivatized with one or more compounds selected from the group consisting of iminodiacetic acid (IDA) or nitrilotriacetic acid (NTA) linked to dicatonic metals selected from the group consisting of nickel (Ni), cobalt (Co) or copper (Cu); tertiary or quaternary amines selected from the group consisting of the diethylaminoethanol (DEAE) and trimethyl ammonium (QAE); glutathione; amylase; avidin; streptavidin; calmodulin; protein A; and protein G.

8. The method for preserving tagged peptides or proteins according to claim 1, wherein the matrix is derivatized with iminodiacetic acid (IDA) or nitrilotriacetic acid (NTA) attached to dicatonic metals selected from the group consisting of nickel (Ni), cobalt (Co), and copper (Cu).

9. The method for preserving tagged peptides or proteins according to claim 1, wherein the matrix is derivatized with tertiary or quaternary amines selected from the group consisting of the diethylaminoethanol (DEAE) and trimethyl ammonium (QAE).

10. The method for preserving tagged peptides or proteins according to claim 1, wherein said tagged peptides or proteins comprise tags selected from the group consisting of Histidine tags (Histag), domains of choline binding (Lytag), glutathione S-transferase (GST-tag), maltose binding protein (MBP-tag), biotin or Strep-tag, calmodulin binding domain (CBD-tag), calmodulin binding protein (CBP-tag), calmodulin regulated proteins, and total or partial sequences of immunoglobulin heavy chains.

11. The method for preserving tagged peptides or proteins according to claim 1, wherein said tagged peptides or protein comprise histidine tags (Histag).

12. The method for preserving tagged peptides or proteins according to claim 1, wherein said tagged peptides or protein comprise domains of choline binding (Lytag).

13. The method for preserving tagged peptides or proteins according to claim 1, further comprising transporting the partially or totally dried matrix comprising the tagged peptide or protein to another laboratory or technical center without requiring refrigeration between steps (d) and (e).

14. The method for preserving tagged peptides or proteins according to claim 1, further comprising transporting the partially or totally dried matrix comprising the tagged peptide or protein to another laboratory or technical center without requiring refrigeration between steps (d) and (e), wherein said tagged peptides or protein comprises histidine tags (Histag).

15. The method for preserving tagged peptides or proteins according to claim 1, further comprising transporting the partially or totally dried matrix comprising the tagged peptide or protein to another laboratory or technical center without requiring refrigeration between steps (d) and (e), wherein said tagged peptides or protein comprises domains of choline binding (Lytag).

* * * * *